United States Patent [19]

Maryanoff et al.

[11] Patent Number: 4,582,916

[45] Date of Patent: Apr. 15, 1986

[54] CHLOROSULFATE AND AZIDOSULFATE ESTERS OF TETRAHYDRO-2H-PYRAN-2-YL-METHANOL

[75] Inventors: Bruce E. Maryanoff, New Hope; Joseph F. Gardocki, Doylestown, both of Pa.

[73] Assignee: McNeilab, Inc., Fort Washington, Pa.

[21] Appl. No.: 700,147

[22] Filed: Feb. 11, 1985

Related U.S. Application Data

[62] Division of Ser. No. 535,475, Sep. 26, 1983, Pat. No. 4,513,006.

[51] Int. Cl.$^4$ .................. C07D 311/94; C07D 309/06
[52] U.S. Cl. ........................... 549/387; 549/426; 549/427; 549/396; 549/338; 549/337; 536/122
[58] Field of Search ............... 549/426, 427, 387, 396, 549/337, 338; 536/54, 122

[56] References Cited

U.S. PATENT DOCUMENTS 4,075,351  2/1978  Hirsch ............................. 424/303

OTHER PUBLICATIONS

Hedayatullah et al., *Tet. Lett.*, No. 29, pp. 2455–2458, 1975.

N. K. Kochetkov, et al. in *Zhurnal Obshchei Khimii*, vol. 41, No. 8, pp. 1866–1871, (1971).
N. K. Kochetkov, et al. in *Journal of General Chemistry of the USSR* 42 (12), 2755–2757, (1972); and 44 (4) 871–875 (1974).
N. K. Kochetkov, et al. in *Doklady Akademii Nauk SSSR*, vol. 216, No. 1, pp. 97–100, (1974).
*Tetrahedron Letters*, No. 36, pp. 3365–3368, Pergamon Press Ltd., (1978), by T. Tsuchiya.
*J. Med. Chem.*, 1981, 24, 901–903, A. F. Hirsch.

*Primary Examiner*—Nicky Chan
*Attorney, Agent, or Firm*—David J. Levy

[57] ABSTRACT

Sulfamates of the following formula (I):

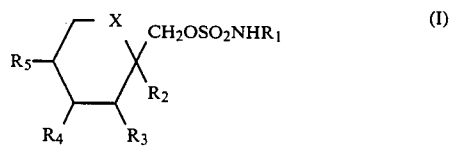

wherein X is O or $CH_2$ and $R_1$, $R_2$, $R_3$, $R_4$ and $R_5$ are as herein defined have been found to exhibit anticonvulsant activity and are thus useful in the treatment of conditions such as epilepsy. Further, pharmaceutical compositions containing a compound of formula (I) as well as methods for their use and intermediates form part of the present invention.

8 Claims, No Drawings

CHLOROSULFATE AND AZIDOSULFATE ESTERS OF TETRAHYDRO-2H-PYRAN-2-YL-METHANOL

This is a division of application Ser. No. 535,475, filed Sept. 26, 1983, now U.S. Pat. No. 4,513,006.

Sulfamates of various structures, including those derived from monosaccharides are described in references such as N. K. Kochetkov et al in *Zhurnal Obshchei Kimmii*, Vol. 41, No. 8, 1866 to 1871 (1971), Vol. 42, No. 12, 2755 to 2757 (1972) and Vol. 44, No. 4, 871 to 875 (1974) and in *Doklady Akademii Nauk SSR*, Vol. 216, No. 1, 97 to 100 (1974); T. Tsuchiya et al., in *Tetrahedron Letters*, No. 36, 3365 to 3368 (1978); and A. F. Hirsch in *Journal of Medicinal Chemistry*, 24, 901 to 903 (1981) and U.S. Pat. No. 4,075,351.

SUMMARY OF THE INVENTION

It has been found that sulfamates of the following formula (I):

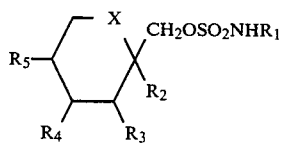

wherein X is O or $CH_2$ and $R_1$, $R_2$, $R_3$, $R_4$ and $R_5$ are as hereinafter defined, possess anticonvulsant activity in mammals and are thus useful in treating disease states such as epilepsy and glaucoma. Also part of the present invention are pharmaceutical compositions containing one or more sulfamates of formula (I) as well as methods for the treatment e.g., prevention, of convulsions using such compositions.

DETAILED DESCRIPTION OF THE INVENTION

The sulfamates of the invention are of the following formula (I):

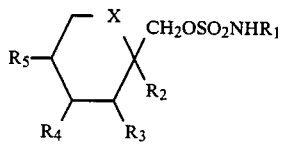

wherein
X is $CH_2$ or oxygen;
$R_1$ is hydrogen or alkyl; and
$R_2$, $R_3$, $R_4$ and $R_5$ are independently hydrogen or lower alkyl and, when X is $CH_2$, $R_4$ and $R_5$ may be alkene groups joined to form a benzene ring and, when X is oxygen, $R_2$ and $R_3$ and/or $R_4$ and $R_5$ together may be a methylenedioxy group of the following formula (II):

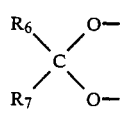

wherein $R_6$ and $R_7$ are the same or different and are hydrogen, lower alkyl or are alkyl and are joined to form a cyclopentyl or cyclohexyl ring.

$R_1$ in particular is hydrogen or alkyl of about 1 to 4 carbons, such as methyl, ethyl and iso-propyl. Alkyl throughout this specification includes straight and branched chain alkyl. Alkyl groups for $R_2$, $R_3$, $R_4$, $R_5$, $R_6$ and $R_7$ are of about 1 to 3 carbons and include methyl, ethyl, iso-propyl and n-propyl. When X is $CH_2$, $R_4$ and $R_5$ may combine to form a benzene ring fused to the 6-membered X-containing ring, i.e., $R_4$ and $R_5$ are defined by the alkatrienyl group $=CH-CH=CH-CH=$.

A particular group of compounds of formula (I) is that wherein X is oxygen and both $R_2$ and $R_3$ and $R_4$ and $R_5$ together are methylenedioxy groups of the formula (II) wherein $R_6$ and $R_7$ are both hydrogen, both alkyl or combine to form a spiro cyclopentyl or cyclohexyl ring, in particular where $R_6$ and $R_7$ are both alkyl such as methyl. A second group of compounds is that wherein X is $CH_2$ and $R_4$ and $R_5$ are joined to form a benzene ring. A third group of compounds of formula (I) is that wherein both $R_2$ and $R_3$ are hydrogen.

The compounds of formula (I) may be synthesized by the following methods:

(a) Reaction of an alcohol of the formula $RCH_2OH$ with a chlorosulfamate of the formula $ClSO_2NH_2$ or $ClSO_2NHR_1$ in the presence of a base such as potassium t-butoxide or sodium hydride at a temperature of about $-20°$ to $25°$ C. and in a solvent such as toluene, THF or dimethylformamide wherein R is a moiety of the following formula (III):

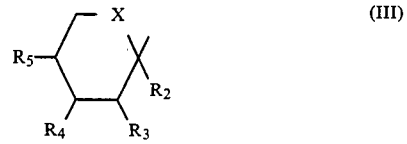

(b) Reaction of an alcohol of the formula $RCH_2OH$ with sulfurylchloride of the formula $SO_2Cl_2$ in the presence of a base such as triethylamine or pyridine at a temperature of about $-40°$ to $25°$ C. in a solvent such as diethyl ether or methylene chloride to produce a chlorosulfate of the formula $RCH_2OSO_2Cl$.

The chlorosulfate of the formula $RCH_2OSO_2Cl$ may then be reacted with an amine of the formula $R_1NH_2$ at a temperature of about $-40°$ to $25°$ C. in a solvent such as methylene chloride or acetonitrile to produce a compound of formula (I). The reaction conditions for (b) are also described by T. Tsuchiya et al in *Tet. Letters*, No. 36, p. 3365 to 3368 (1978).

(c) Reaction of the chlorosulfate $RCH_2OSO_2Cl$ with a metal azide such as sodium azide in a solvent such as methylene chloride or acetonitrile yields an azidosulfate of the formula $RCH_2OSO_2N_3$ as described by M. Hedayatullah in *Tet. Lett.* p. 2455-2458 (1975). The azidosulfate is then reduced to a compound of formula (I) wherein $R_1$ is hydrogen by catalytic hydrogenation, e.g. with a noble metal and $H_2$ or by heating with copper metal in a solvent such as methanol.

The starting materials of the formula $RCH_2OH$ may be obtained commercially or as known in the art. For example, starting materials of the formula $RCH_2OH$ wherein both $R_2$ and $R_3$ and $R_4$ and $R_5$ are idential and are of the formula (II) may be obtained by the method of R. F. Brady in *Carbohydrate Research*, Vol. 15, p. 35 to 40 (1970) or by reaction of the trimethylsilyl enol ether of a $R_6COR_7$ ketone or aldehyde with fructose at a temperature of about 25° C. in a solvent such as a halocarbon, e.g. methylene chloride in the presence of a protic acid such as hydrochloric acid or a Lewis Acid such as zinc chloride. The trimethylsilyl enol ether reaction is described by G. L. Larson et al in *J. Org. Chem.* Vol. 38, No. 22, p. 3935 (1973).

Further, carboxylic acids and aldehydes of the formulae RCOOH and RCHO may be reduced to compounds of the formula $RCH_2OH$ by standard reduction techniques, e.g. reaction with lithium aluminum hydride, sodium borohydride or borane-THF complex in an inert solvent such as diglyme, THF or toluene at a temperature of about 0° to 100° C., e.g., as described by H. O. House in "Modern Synthetic Reactions", 2nd Ed., pages 45 to 144 (1972).

The compounds of the invention include the various individual isomers as well as the racemates thereof, e.g., the various alpha and beta attachments, i.e., below and above the plane of the drawing, of $R_2$, $R_3$, $R_4$ and $R_5$ on the 6-membered ring. Preferably, the oxygens of the methylenedioxy group (II) are attached on the same side of the 6-membered ring.

The compounds of formula (I) are useful as anticonvulsant agents. The anticonvulsant activity of the subject compounds was determined using a standard "maximal electroshock test" (MES). In this test, activity is indicated by a block of the tonic extensor seizure caused by application of an electric shock to mice via corneal electrodes, as described by Swinyard et al in *J. Pharmacol. Exptl. Therap.* 106, 319 (1952), and recorded as % block. A more recent description of current anticonvulsant drug screening is given in Swinyard et al in *Epilepsia* 19, 409 (1978).

The anticonvulsant activity of compounds of this invention tested according to the Swinyard (1952) method is shown in the following Table I:

TABLE I

| Example | Compound | MES test $ED_{50}$ *(mg/kg, i.p.) |
|---|---|---|
| 1 | 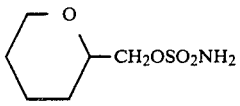 | 195 |
| 2 | 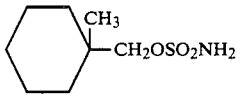 | 270 |
| 3 | 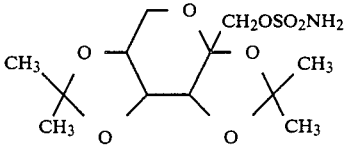 | 26 |
| 4 | 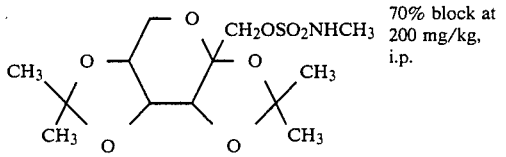 | 70% block at 200 mg/kg, i.p. |

TABLE I-continued

| Example | Compound | MES test $ED_{50}$ *(mg/kg, i.p.) |
|---|---|---|
| 5 | 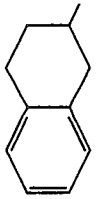 | 55 |

*Unless otherwise noted.

For treating epilepsy, a compound of formula (I) may be employed at a daily dosage in the range of about 30 to 2000 mg, usually in 2 to 4 divided doses, for an average adult human. A unit dose would contain about 10 to 500 mg of the active ingredient.

In general, compounds of formula (I) may be used in treating epilepsy in a manner similar to that used for phenytoin. Medical aspects of the treatment of epilepsy are described by L. S. Goodman et al in "The Pharmacological Basis of Therapeutics", 5th Ed. pages 201 to 216, Macmillan (1975).

Further, compounds of formula (I) are inhibitors of carbonic anhydrase, as determined by the methods described by S. J. Dodgson et al in the *Proc. Natl. Acad. Sci.*, U.S.A., 77, pages 5562 to 5566 (1980) or by N. Itada et al in the *Journal Biol. Chem.*, 252, pages 3881 to 3890 (1977) and as such, are useful in the treatment of glaucoma. The relationship between the treatment of glaucoma and carbonic anhydrase inhibition is described by A. Stein et al in the *American Journal of Opthalmology*, 95:222-228 (1983). For the treatment of glaucoma, a compound of formula (I) may be administered systemically, e.g. by oral or parenteral routes as described below, or topically in the eye in a mineral oil solution or suspension, or aqueous suspension. When used systemically, the compound would be administered in an amount of about 50 to 500 mg per day for an average adult human, while the topical dosage would be about 1 to 3 drops (per eye) of a solution or suspension containing about 1 to 5% by weight of a compound of formula (I) with the dosage being adminstered about 1 to 4 times per day.

To prepare the pharmaceutical compositions of this invention, one or more sulfamate compounds of formula (I) are intimately admixed with a pharmaceutical carrier according to conventional pharmaceutical compounding techniques, which carrier may take a wide variety of forms depending on the form of preparation desired for administration, e.g., oral, by suppository, or parenteral. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations. such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

The pharmaceutical compositions herein will contain, per dosage unit e.g., tablet, capsule, powder, injection, teaspoonful, suppository and the like, from about 10 to about 500 mg of the active ingredient.

The foregoing compositions are particularly suitable for use in the treatment of epilepsy or the symptoms of epilepsy by a method comprising internally administering to a subject suffering from the symptoms of epilepsy compositions comprising an effective epilepsy inhibiting amount of a compound of formula (I).

Also part of the present invention are intermediates of the formulae $RCH_2OSO_2Cl$ and $RCH_2OSO_2N_3$.

In the following Examples and throughout the specification the following abbreviations may be used: g (grams); ml (milliliters); min (minutes); hr (hours); mol (moles); cm (centimeters); v/v (volume to volume); mp (melting point); TLC (thin layer chromatography); NMR (nuclear magnetic resonance); IR (infrared); DMF (dimethylformamide); THF (tetrahydrofuran); and C, H, N, etc. (the chemical symbols for the elements).

EXAMPLE 1

(Tetrahydro-2H-pyran-2-yl)methane sulfamate

To a cold solution (−5° C.) of tetrahydropyran-2-methanol (2.33 g, 0.02 mol) in DMF (40 ml) was added 50% oily sodium hydride (1.17 g, 0.024 mol as NaH). After stirring for 45 min, sulfamoyl chloride (3.42 g, 0.03 mol) was added and the stirring continued for an additional 45 min, at −5° C. The reaction mixture was poured into cold water and extracted with chloroform. The organic layer was dried ($Na_2SO_4$) and the solvents were removed under vacuum to give a syrup which was dry column chromatographed (eluted with ethyl acetate:hexane, 4:1 v/v) to give pure (tetrahydro-2H-pyran-2-yl) methanesulfamate as a pale yellow syrup, IR:($CHCl_3$) 1180 cm$^{-1}$ and 1370 cm$^{-1}$ ($OSO_2NH_2$).

EXAMPLE 2

(1-Methylcyclohexyl)methane sulfamate

To a cold solution (−4° C.) of (1-methylcyclohexyl)methanol (6.2 g, 0.048 mol) in DMF (90 ml) was added 50% oily sodium hydride (2.81 g, 0.059 mol as NaH). After stirring for 1 hr, sulfamoyl chloride (7.82 g, 0.062 mol) was added and the stirring was continued for an additional 30 min at −4° C. The reaction mixture was poured into cold water and extracted with toluene. The organic layer was dried ($Na_2SO_4$) and the solvents were removed under vacuum to give a syrup which crystallized upon cooling. Recrystallization from chloroform/hexane gave pure (1-methylcyclohexyl)methane sulfamate, mp 40°–42° C.

EXAMPLE 3

2,3:4,5-Bis-O-(1-methylethylidene)-β-D-fructopyranose sulfamate

To a cold solution (−4° C.) of 2,3:4,5-di-O-isopropylidene-β-D-fructopyranose (75 g, 0.29 mol) in DMF (725 ml) was added 50% oily sodium hydride (16.34 g, 0.34 mol as NaH). After stirring for 90 min, sulfamoyl chloride (54.9 g, 0.48 mol) was added and the stirring continued for an additional 3.5 hr at that temperature. The reaction mixture was poured into cold water and extracted with toluene. The organic layer was dried ($Na_2SO_4$) and the solvents removed under vacuum to give a syrup which crystallized immediately. Recrystallization from ethylacetate/hexane gave pure 2,3:4,5-bis-O-methylethylidene)-β-D-fructopyranose sulfamate, mp 125°–126° C.

EXAMPLE 4

2,3:4,5-Bis-O-(1-methylethylidene)-β-D-fructopyranose methyl sulfamate

A solution of sulfonyl chloride (93 ml, 1.15 mol) in methylene chloride (100 ml) was added dropwise to a cold solution (−35° C.) of 2,3:4,5-di-O-isopropylidene-β-D-fructopyranose (150 g, 0.58 mol) in methylene chloride (400 ml) and pyridine (150 ml). The reaction mixture was allowed to stir and warm to room temperature (25° C.); it was stirred for an additional 2 hr. Solvents were removed under vacuum. The resulting semi-solid was dissolved in anhydrous acetonitrile (35 g, 150 ml) and methyl amine was bubbled in. The reaction mixture was tightly stoppered and solvents removed under vacuum. The resulting syrup was subjected to liquid chromatography (dry column ethyl acetate:hexane, 4:1) yielding a light yellow syrup, 2,3:4,5-bis-O-(1-methylethylidene)-β-D-fructopyranose methylsulfamate, which was homogeneous by TLC and $^1$H NMR.

EXAMPLE 5

(1,2,3,4-Tetrahydro-2-naphthalenyl)methyl sulfamic acid ester

To a cold solution (−5°) of (1,2,3,4-tetrahydro-2-naphthalenyl)methanol (7.1 g, 0.044 mol) in DMF (80 ml) was added 50% oily sodium hydride (2.56 g, 0.054 mol as NaH). After stirring for 45 min, sulfamoyl chloride (6.6 g, 0.057 mol) was added and the stirring continued for an additional 95 min at −5° C. The reaction mixture was poured into cold water and extracted with toluene. The organic layer was dried ($Na_2SO_4$) and the solvents removed under vacuum to give a syrup which crystallized immediately. Recrystallization from chloroform/hexane gave pure (1,2,3,4-tetrahydro-2-naphthalenyl)methyl sulfamic acid ester, mp 108°–109° C., as a white solid.

What is claimed is:

1. A chlorosulfate of the formula $RCH_2OSO_2Cl$ or an azidosulfate of the formula $RCH_2OSO_2N_3$ wherein R is of the following formula (III):

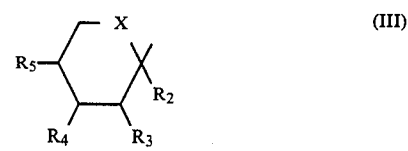

wherein
X is oxygen
$R_2$, $R_3$, $R_4$ and $R_5$ are independently hydrogen or lower alkyl and $R_2$ and $R_3$ and/or $R_4$ and $R_5$ together may be a group of the following formula (II):

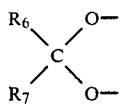 (II)

wherein
R$_6$ and R$_7$ are the same or different and are hydrogen, lower alkyl or are alkyl and are joined to form a cyclopentyl or cyclohexyl ring.

2. The compound of claim 1, wherein said compound is of the formula RCH$_2$OSO$_2$Cl.

3. The compound of claim 1, wherein said compound is of the formula RCH$_2$OSO$_2$N$_3$.

4. The compound of claim 1, wherein
X is oxygen: and
R$_2$ and R$_3$ and R$_4$ and R$_5$ together are groups of the formula (II).

5. The compound of claim 1 wherein
X is oxygen; and
R$_2$ and R$_3$ and R$_4$ and R$_5$ together are groups of the formula (II) wherein R$_6$ and R$_7$ are methyl.

6. The compound of claim 5 wherein said compound is of the formula RCH$_2$OSO$_2$Cl.

7. The compound of claim 1, wherein said lower alkyl group for R$_2$, R$_3$, R$_4$ and R$_5$ is alkyl of about 1 to 3 carbons; and said lower alkyl for R$_6$ and R$_7$ is alkyl of about 1 to 3 carbons.

8. The compound of claim 5 wherein said compound is of the formula RCH$_2$OSO$_2$N$_3$.

* * * * *